(12) United States Patent
Shoham et al.

(10) Patent No.: US 11,141,227 B2
(45) Date of Patent: Oct. 12, 2021

(54) SURGICAL ROBOTIC SYSTEM

(71) Applicant: MAZOR ROBOTICS LTD., Caesarea (IL)

(72) Inventors: Moshe Shoham, Hoshaya (IL); Eliyahu Zehavi, Haifa (IL); Yossi Bar, Haifa (IL)

(73) Assignee: MAZOR ROBOTICS LTD., Caesarea (IL)

( * ) Notice: Subject to any disclaimer, the term of this patent is extended or adjusted under 35 U.S.C. 154(b) by 0 days.

(21) Appl. No.: 16/068,947

(22) PCT Filed: Jan. 11, 2017

(86) PCT No.: PCT/IL2017/050036
§ 371 (c)(1),
(2) Date: Jul. 10, 2018

(87) PCT Pub. No.: WO2017/122202
PCT Pub. Date: Jul. 20, 2017

(65) Prior Publication Data
US 2019/0117320 A1    Apr. 25, 2019

Related U.S. Application Data

(60) Provisional application No. 62/277,114, filed on Jan. 11, 2016.

(51) Int. Cl.
*A61B 34/30* (2016.01)
*A61B 90/50* (2016.01)
(Continued)

(52) U.S. Cl.
CPC .............. *A61B 34/30* (2016.02); *A61B 90/50* (2016.02); *A61F 2/4455* (2013.01);
(Continued)

(58) Field of Classification Search
CPC .................... A61B 34/30–77; A61F 2/44–447
See application file for complete search history.

(56) References Cited

U.S. PATENT DOCUMENTS 4,756,662 A * 7/1988 Tanie ........................ B25J 9/06
414/729
4,921,393 A * 5/1990 Andeen .............. B23Q 11/0014
414/729

(Continued)

FOREIGN PATENT DOCUMENTS

CN    101224574    7/2008
CN    101919739    12/2010
(Continued)

OTHER PUBLICATIONS

Drazin et al., "Simultaneous Lateral Interbody Fusion and Posterior Percutaneous Instrumentation: Early Experience and Technical Considerations", Biomed Research International, vol. 2015, article ID 458284, available for download at http://dx.doi.org/10.1155/2015/458284.

(Continued)

*Primary Examiner* — Nicholas J Plionis
(74) *Attorney, Agent, or Firm* — Sheridan Ross P.C.

(57) ABSTRACT

A surgical robot system whose robotic arm is divided into two parts, and is connected to the patient at the junction of the two parts, by means of a bone connector. The section between the bone connector and the robotic base has a predetermined level of flexibility, enabling the bone connector limited movement. Consequently, the patient's body can also move without the bone connector exerting excess forces on the patient, and without detachment from the patient. The arm section between the bone connection link and the end actuator has high rigidity, such that the pose of the end actuator relative to the patient is accurately maintained. As the patient undergoes small movements, such as (Continued)

in breathing or coughing, the bone connector and base connection arm section, move together with motion of the patient's bone, while the pose of the end actuator relative to the patient is accurately maintained.

26 Claims, 4 Drawing Sheets (51) Int. Cl.
*A61F 2/44* (2006.01)
*A61F 2/46* (2006.01)
*A61B 17/00* (2006.01)
*A61B 90/00* (2016.01)
*A61F 2/30* (2006.01)

(52) U.S. Cl.
CPC ... *A61F 2/4611* (2013.01); *A61B 2017/00694* (2013.01); *A61B 2017/00699* (2013.01); *A61B 2090/064* (2016.02); *A61F 2002/30622* (2013.01); *A61F 2002/4632* (2013.01)

(56) References Cited

U.S. PATENT DOCUMENTS

| | | | | |
|---|---|---|---|---|
| 5,806,518 | A * | 9/1998 | Mittelstadt | A61F 2/30942 600/407 |
| 6,322,567 | B1 * | 11/2001 | Mittelstadt | A61B 34/70 606/130 |
| 8,518,051 | B2 | 8/2013 | Shoham et al. | |
| 8,571,638 | B2 | 10/2013 | Shoham | |
| 8,795,335 | B1 * | 8/2014 | Abdou | A61B 17/7065 606/247 |
| 8,838,205 | B2 | 9/2014 | Shoham et al. | |
| 2010/0234856 | A1 * | 9/2010 | Stoianovici | A61B 34/70 606/130 |
| 2011/0106102 | A1 * | 5/2011 | Balicki | A61B 3/1005 606/130 |
| 2014/0316436 | A1 * | 10/2014 | Bar | A61B 17/1757 606/130 |
| 2015/0045813 | A1 * | 2/2015 | Kostrzewski | A61B 17/86 606/130 |
| 2016/0184033 | A1 * | 6/2016 | Cooper | A61B 34/30 606/130 |
| 2017/0156808 | A1 * | 6/2017 | Auld | A61B 34/77 |
| 2017/0258535 | A1 * | 9/2017 | Crawford | A61B 17/7082 |
| 2017/0360512 | A1 * | 12/2017 | Couture | A61B 17/1675 |

FOREIGN PATENT DOCUMENTS

| | | |
|---|---|---|
| CN | 104602635 | 5/2015 |
| CN | 104736095 | 6/2015 |
| CN | 104758055 | 7/2015 |
| JP | 2004154174 A | 6/2004 |
| WO | WO 2013/079843 | 6/2013 |
| WO | 2015023853 A1 | 2/2015 |
| WO | 2015/087335 A1 | 6/2015 |

OTHER PUBLICATIONS

European Supplemental Search Report and Written Opinion of EP application 17738286.8 dated Jul. 12, 2019.
Kaneko H et al. "Breathing movements of the chest and abdominal wall in healthy subjects." Resp Care vol. 57, No. 9, Sep. 1, 2012, pp. 1442-1451.
Official Action with English Translation for China Patent Application No. 201780010636.6, dated Aug. 4, 2020, 19 pages.
Official Action with English Translation for China Patent Application No. 201780010636.6, dated Mar. 30, 2021, 14 pages.

* cited by examiner

SURGICAL ROBOTIC SYSTEM

FIELD OF THE INVENTION

The present invention relates to the field of robotic systems for executing surgical procedures on a patient over a significant range of locations on the patient's body, without small motions of the patient reducing the accuracy of placement of the surgical tool, especially for use in orthopedic surgery.

BACKGROUND

In U.S. Pat. No. 8,571,638 for "Miniature Bone-Attached Surgical Robot" to M. Shoham, a co-inventor of the present application, there is described a miniature bone mounted surgical robot, which by virtue of it being mounted on the subject's bone, in combination with the small size of the robot, ensures that the robotic arm, when actuated to an intended pose, maintains that position precisely relative to the bone of the subject on which the robot is mounted. This situation is achieved because of the rigid attachment of the robot base to the subject's bone.

The miniature bone mounted surgical robot has many advantages when surgery is performed over a reasonably limited region of the subject's body, as evidenced by a number of patent applications and granted patents for various applications of the bone mounted robot, such as U.S. Pat. No. 8,838,205 for "Robot for use with Orthopedic Inserts", and U.S. Pat. No. 8,518,051 for "Robotic Total/Partial Knee Arthroplastics", both having a common inventor with the present application, and others. However this system may have disadvantages when surgery is to be performed over larger areas of the subject's body, since a miniature robot that can be bone mounted inevitably has a limited operating envelope. A robotic system which enables a large range of access, without losing the substantial advantages of bone attachment, and without the need for release and reattachment at several locations, would be desirable.

In the prior art, such as in U.S. Pat. No. 5,806,518 to B. Mittelstadt, for "Method and System for Positioning Surgical Robot", there is described a robotic surgical system in which the subject's bone is rigidly fixed relative to the base of the bed or floor mounted surgical robot. Other systems exist in which the subject's bone is attached to a position monitoring fixture, such that motion of the bone is transferred with a 1 to 1 relationship to the system controller, such that compensation can be made for any bone motion occurring. However, such systems may be considered to be large and cumbersome, and require additional active control functions for monitoring the bone position.

There therefore exists a need for a robotic surgical system which overcomes at least some of the disadvantages of prior art systems and methods.

The disclosures of each of the publications mentioned in this section and in other sections of the specification, are hereby incorporated by reference, each in its entirety.

SUMMARY

The present disclosure describes a new surgical robotic system having a large working envelope, which provides a defined and precise relationship between the position of the robot's end actuator, and the subject's anatomy parts on which a tool held by the end actuator is intended to operate. At the same time, the system allows the subject to undergo limited movements, such as those related to breathing or to motion due to pressure by the surgeon, without exerting undue constraint on the subject, and without breaking the accurately defined spatial location and orientation of the end actuator relative to the body part on which it is operating. In the currently described systems, the robotic arm is anchored to the body part by means of a connection element, which is generally rigid, but can optionally have controllable and monitored extension and contraction features. Using the example of a system operating in the region of the upper body section of a subject, the extent of motion of the subject's thoracic spine or sternum because of the subject's breathing or coughing, is generally no more than the order of 10 to 12 mm, though larger motion is possible. All robotic arms have a certain intrinsic level of flexibility. However, in prior art systems, in order to maintain the accuracy of the robotic motion, such flexibility is generally aimed at being as limited as possible, by using links and joint configurations with the maximum level of rigidity commensurate with the robot's dimensions and weight.

The present system differs from such prior art systems in that a part of the robotic arm may be constructed having a predetermined increased level of flexibility, such that despite the connection of the arm to the subject's body part, that section of the robotic arm from the base of the robot to the connection of the arm to the body part, can absorb limited motion of the subject, without subjecting the subject's body to excess pressure, and without the connection from the robotic arm to the body part becoming detached. This predetermined increased level of flexibility is enabled by appropriate selection of the structure of the robotic links and of the joints between the connection to the subject's body part and the base of the robot, whether in the mechanical stiffness of the arm links themselves, or in the level of the stiffness of the joints in the arm resulting from the joint control law utilized. The flexibility of the robotic base arm should be such as to compensate for patient motion, and may be modelled as a series of "springs", some of which represent the robotic base arm links, and some of which represent the robotic base arm joints.

On the other hand, the robotic actuation arm, from the point of its attachment to the body connection unit, up to the robotic end actuator, is characterized to be maximally rigid, with as little free motion as is possible, so that the position of the robotic end actuator is precisely known relative to the body connection unit. This rigid robotic actuation arm includes arm or link or strut elements, and rotary or prismatic joints between the body connection point and the end actuator. In order to simplify nomenclature, the robotic connecting links and joints between the connection to the subject's body part and the base of the robot, are known hereinbelow as the "robotic base arm", while the total robotic actuation arm or arms from the point of their connection to the bone connector to the robotic end actuator, are known hereinbelow as the "robotic actuator arm". The links of the robotic actuator arm and their associated joints are therefore constructed to have the highest accuracy and rigidity achievable, commensurate with any size or weight limitations imposed upon the robotic actuator arm by virtue of the environment in which the surgical robotic system is to operate, and the cost effectiveness and convenience of the construction of the structure.

In robotic arm construction, the links have a level of deformability, which is dependent on their mechanical structure, while the joint controllers are generally designed to have as small a tracking error as possible in order to maintain accuracy. However, according to further exemplary implementations of the presently described systems, while the links of the robotic base arm are constructed to have a predetermined level of flexibility, the joint stiffness can be made controllable, by selecting the tightness of the electronic feedback loop used to control the joint position. This latter effect enables the provision of a variable stiffness robotic base arm, such that the flexibility of the robotic base arm can be adjusted electronically. This feature provides a number of advantages to such an implementation. Firstly, the stiffness of the robotic base arm can be electronically adjusted according to the motion expected of the patient at the attachment point of the connection element. Thus, for a corpulent patient, or a patient breathing heavily, where a larger motion may be expected, the robotic base arm flexibility could be increased. Where little motion is expected, such as with a lightly breathing subject, or where the connection is attached to an anatomic part remote from the chest of the subject, the flexibility could be reduced.

Secondly, the robotic base arm stiffness can be adjusted according to the pose or configuration of the robotic base arm. This feature may be important because of the different levels of flexibility which may be desired when the robotic base arm is extended to reach a subject connection point distant from the base, as compared with a patient lying in a position with the connection point disposed close to the base, and hence requiring the robotic base arm to be in a significantly folded configuration.

The position and orientation of the robotic end effector of the system can be related to the anatomy of the subject, and hence, by image comparison, to any preoperative images of the subject's anatomy, by registration methods known in the art. A particularly convenient method is to attach a target having radio-opaque markers arranged in a known three dimensional pattern, to the end effector, and to generate one or more images of the subject's anatomy including the target, while the robotic settings of the pose, namely, the position and orientation of the end actuator, is known. Such an image or images can be used to uniquely define the intraoperative co-ordinate system of the robotic end actuator relative to the subject's anatomy, and comparison of the anatomic features of the intraoperative image(s) with those of the preoperative images enables the robotic co-ordinate system to be registered to the preoperative images of the subject's anatomy, such that the robotic end effector can now be directed to perform the preoperative surgical plan. Obviously, this registration procedure and the subsequent robotic-guided surgical procedure, is only effective because the intraoperative position of the end effector relative to the subject's anatomy is well defined by the robotic control system, because of the high level of rigidity of the robotic actuator arm of the present system.

The most commonly used anatomical parts of the subject on which the present systems will advantageously be used, are bones, and to simplify the text, this disclosure will refer to the example of a bone connection as the dominant method of using the systems, though it is to be understood that this is not intended to limit the systems in any way, subject to being able to attach the connection element to the subject's anatomical part in a secure manner.

Using the example of a bone connection in the upper body section of the subject, the free motion of the subject's sternum or thoracic spine may be restrained to a certain level by the use of these systems, and such restraining should be such as not to exert undue discomfort on the subject. However, in order to enable the subject's body to undertake larger motions than are enabled by the flexibility of the robotic base arm, the surgical robotic systems of the present disclosure can optionally be equipped with a device such as that described in the PCT application entitled "Semi-Rigid Bone Attachment Robotic Surgery System" published as WO2015/087335. There is described therein a bone connection system for attaching a bone of the subject to a surgical robot having its base mounted in the vicinity of the subject, such as on the bed or on the floor. The system incorporates a switchable bone connection unit attached between the subject's bone and a selected support point, for example, at the connecting link between the robotic base arm and the robotic actuator arm. This unit has a locked state in which the bone is attached essentially rigidly to the support point, and a released state in which the bone can move relative to the support point. The unit comprises a force sensor for determining the force exerted between the bone and the support point of the robot, and a position sensor for measuring the position of the bone relative to the support point of the robot while the unit is in its released state. The unit switches from its locked state to its released state when the force exceeds a predetermined level, selected to ensure that the bone can move without becoming detached from its bone connection element, and that the rigidity of the static connection does not exert undue discomfort on the patient. A measurement device should be included so that the robotic control system can monitor the operation of the bone attachment unit, such that the known position of the robot actuating arm relative to the bone can be maintained, by appropriate adjustment of the robot actuating arm. When such a bone connection unit is incorporated into the presently described systems, it comes into operation sequentially, and in addition to, the operation of the increased flexibility of the presently described systems, and without detracting from the operation of the present systems. It thus enable gross movement of the subject's attachment bone without losing the robotic pose reference, whereby those gross movements can be substantially larger than the limited motion which the presently described system is intended to allow.

The systems described in this disclosure may also have a number of additional features providing novel and useful advantages. Because of the increased volumetric envelope of operation, in comparison with bone-mounted robotic systems, the system should incorporate a collision avoidance facility, so that there is no danger of causing harm to the subject by impact with any part of an incorrectly directed robotic arm. This can conveniently be achieved by using an optical scanner which defines the outer envelope of the patient on the operating table, and applies an input signal to the robotic controller to control motion of the robotic actuator arm to prevent such an impact from occurring.

As a further safety feature, the rotary or prismatic joints of the robotic actuator arm may be constructed such that they are back drivable in the event of a power failure or of a controller error, so that the medical personnel can rapidly move the robotic actuator arm by hand to a safe location. Such back driving can be obtained from a number of drive components known in the art, such as the harmonic drive gear.

Another feature, enabled in the present robotic system because of the large envelope of operation, is that the robotic actuator arm can have access to the patient over more than a 90° angle. In such a situation, it becomes possible to perform spinal surgery on a patient lying in a lateral position, with access from both the posterior orientation and the lateral orientation. Such an application has important advantages, since there are spinal operative procedures which are best performed from the lateral approach, such as the XLIF (eXtreme Lateral Interbody Fusion) techniques. Such procedures are most safely and efficiently performed from a lateral approach, thereby evading major blood vessels and abdominal organs, which presented significant challenges in the previously commonly used anterior approach (though it is also possible but uncommon, to use a posterior approach for interbody procedures). On the other hand, other spinal operative procedures are best performed, or even only performable, from the posterior approach, such as the percutaneous insertion of pedicle screws for application of fusion rod's between vertebrae. In the prior art, when both of such procedures had to be performed, it had been the usual practice to do so in two stages with patient repositioning between each stage. The more complex XLIF procedure, involving the insertion of an intervertebral cage, is traditionally performed first with the patient lying in a lateral position. Once completed, if it is necessary to perform additional stabilization using fusion rods fixed between pedicle screws inserted by a percutaneous procedure, the patient has had to be turned on the operating table to a prone position, so that posterior access for the procedure can be more straightforwardly achieved. This requirement arose because it is difficult for the surgeon to perform posterior percutaneous procedures with the patient in the lateral position, mostly because of the difficulty of visualizing and accessing the correct angular approaches from the horizontal orientation. The process of turning and realigning the patient during an operation is a lengthy process and results in a significantly longer operating time, which is both disadvantageous to the patient, and demands more operating room time.

According to a method of the present disclosure, it is possible to perform both of these procedures in a single lateral position. The entire procedure, involving both cage and screw insertion is done with the patient in a lateral position. Once the LIF procedure has been completed, the robotic actuator arm can be repositioned in order to perform the transcutaneous pedicle screw insertion procedure from the posterior approach, but with the patient lying unmoved in the lateral position, using the same initial registration procedure, and without changing the position of the patient. It is to be understood that such a procedure can also be performed by any surgical robotic system having a large enough operating envelope, with or without the bone connection unit and the two part flexibility robotic articulated arm of the present system, and is not intended to be limited to the above described systems of the present disclosure.

There is thus provided in accordance with an exemplary implementation of the systems described in this disclosure, a robotic surgical system, comprising:

(i) a base for fixing the system relative to an operating table, (ii) an end actuator for enabling alignment of a surgical tool for performing a procedure on a subject on the operating table, (iii) a set of robotically actuated arms connected between the base and the end actuator, the set comprising:

a first section connected at one end to the base, and a second section connected to the first section remotely from the end, and having the end actuator at its end region remote from its connection to the first section, and (iv) a connection element coupling a point between the first section and the second section to a part of the subject's anatomy, wherein the mechanical rigidity of the first section is configured to be less than that of the second section.

In any such a system, the mechanical rigidity of the first section may arise at least in part either from a predetermined rigidity of at least one link of the first section, or from the stiffness of at least one joint of the first section. In the latter case, the stiffness of the joint may be adjustable by control of the gain of the electronic feedback controlling the joint. The mechanical rigidity of the first section may then be adjusted electronically according to the expected motion of the part of the subject's anatomy. Alternatively, the mechanical rigidity of the first section may then be adjusted electronically according to the pose of the first section.

Furthermore, in any of the above-described systems, the connection element may be connected to a junction region or a junction between the first section and the second section of the set of robotically actuated arms, or to a component situated between the first section and the second section of the set of robotically actuated arms.

In additional implementations of any of the previously described robotic surgical systems, the first section of the set of robotically actuated arms may have at least one joint configured to have a reduced level of rigidity in comparison with the maximum rigidity attainable in such a type of joint, such that the mechanical rigidity of the first section is less than that of the second section. This reduced level of rigidity may be generated by reducing the gain of the control circuit associated with the joint.

Still other example implementations may involve such a robotic surgical system, but in which the first section of the set of robotically actuated arms may have at least one arm member configured to have a reduced level of stiffness in comparison with the maximum stiffness attainable in such a type of arm member, such that the mechanical rigidity of the first section is less than that of the second section of the set of robotically actuated arms.

Additionally, in the above described robotic surgical systems the second section of the set of robotically actuated arms should have sufficient rigidity that the position of the end actuator relative to the location of the point coupled to the connection element is maintained within a level which is determined to achieve the required accuracy of the surgical procedure.

Any of the above described robotic surgical systems may further comprise an optical scanning system for detection of the subject's body, and a control system inputting the position of the set of robotically actuated arms and of the position of the body in order to prevent collision of the set of robotically actuated arms with the body or with an implantation accessory. In such a system, the optical scanning system may be located either on the set of robotically actuated arms, or an a static point in the vicinity.

According to yet further implementations of the robotic surgical systems described hereinabove, the mechanical rigidity of the first section may be sufficiently less than that of the second section, that the part of the subject's anatomy coupled to the connection element can move by up to the estimated extent of the subject's expected motion, without becoming uncoupled from the connection element. Additionally, the connection element may be switchable between a rigid state and a released state allowing longitudinal extension of the connection element, and the system should then further comprise a force sensor such that the connection element switches from its rigid state to its released state when the force along the connection element exceeds a predetermined level. In that case, the mechanical rigidity of the first section compared to that of the second section should be such that the part of the subject's anatomy coupled to the connection element can move by up to the estimated extent of the subject's expected motion before the connection element switches between its rigid state and its released state. As a specific example, such as a connection to the subject's sternum, the predetermined level of the force may be such that the part of the subject's anatomy coupled to the connection element can move by up to 12 mm before the predetermined level of force is reached. Furthermore, motion of the part of the subject's anatomy coupled to the connection element should be allowed with three directions of freedom. Finally, in any of those implementations incorporating a switchable connection element, the connection element is adapted to reconnect after release, at a known position.

According to yet other implementations described in the present disclosure, there is provided a method of performing spinal surgery on a subject, comprising:

(i) laying the subject in a lateral position on an operating table, (ii) providing a robotic surgical system having an operating envelope that can enable a surgical tool to reach both the lateral side of the subject and the posterior spinal position, (iii) performing a robotic Lateral Interbody Fusion procedure on the subject laying in the lateral position, and (iv) directing the robotic surgical system to perform a percutaneous posterior spinal procedure, wherein both of the procedures are performed without the need to move the subject.

In such a method, the lateral insertion of an intervertebral element and the percutaneous posterior spinal procedure may be robotically performed using a single registration procedure. Furthermore, the robotic surgical system may be attached to an anatomy part of the subject without detachment between the procedures. Finally, the operating envelope may be obtained by use of any of the robotic surgical systems described hereinabove.

BRIEF DESCRIPTION OF THE DRAWINGS

The present invention will be understood and appreciated more fully from the following detailed description, taken in conjunction with the drawings in which.

DETAILED DESCRIPTION

Figure 1:
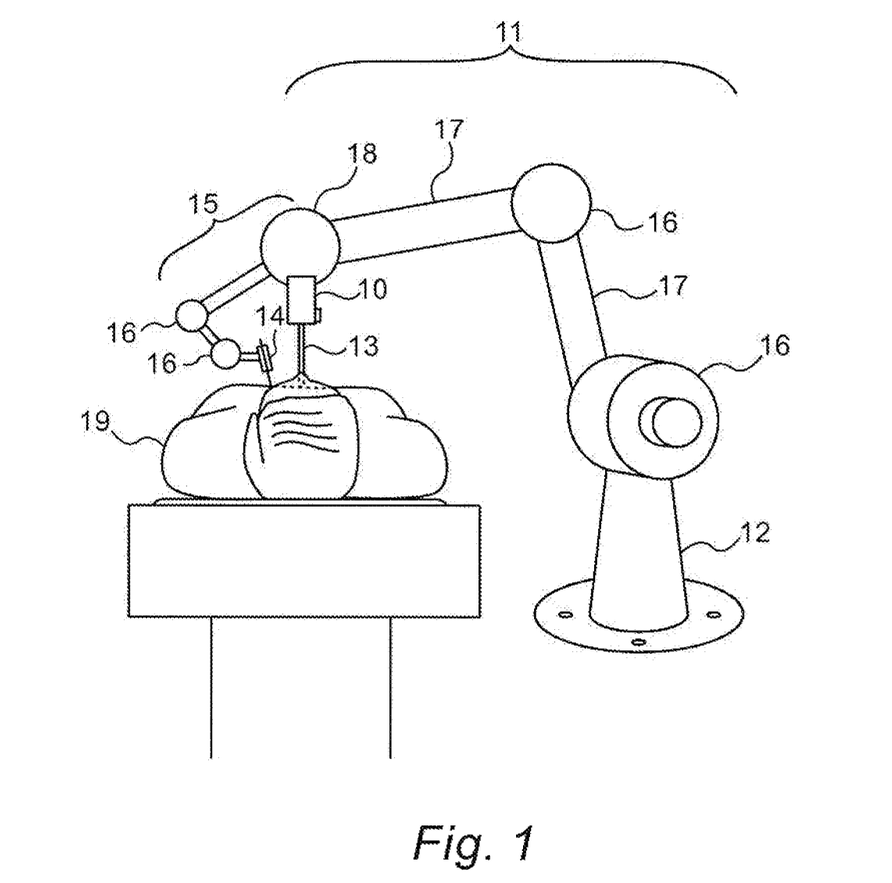
FIG. 1 is a schematic view of a floor mounted surgical robot system of the present disclosure.

Reference is first made to FIG. 1, which is a schematic view of a floor mounted surgical robot system of the present disclosure, the patient 19 is shown lying on the operating table and is attached by means of a bone connection link 13 to an attachment location 18 of the robotic arm. The robotic arm of the system is shown made up of arm parts 17 connected by rotary or prismatic joints 16, and is divided into two parts. The arm section 11, known as the robotic base arm, situated between the bone connection link 13 and the robotic base 12, has a structure such that that section has a predetermined level of flexibility, enabling the bone connection link 13 to move to a limited extent. Consequently, the patient's body can also move to that extent, without exerting excess pressure on the patient, or without the patient becoming unattached from the bone connection link 13. In contrast to that section, the arm section 15 situated between the bone connection link 13 and the end actuator 14 of the robot, known herewithin as the robotic actuator arm, has a high level of rigidity such that the accuracy of the pose of the end actuator 14, relative to the patient's anatomy, is maintained at the highest possible level. Consequently, as the patient's body undergoes small movements, such as generated by breathing or coughing, the bone connection link 13 and the attachment location 18 move together with motion of the patient's bone, thereby accurately maintaining the pose of the end actuator 14 of the robot relative to the attachment location 18 and hence to the patient's body position as it moves. In FIG. 1, the end actuator 14 of the robot is shown as a guide tube holding a surgical tool, though this is understood to be only one example of the use of the end actuator, which could hold a drill, scalpel and any other surgical tool.

Figure 2:
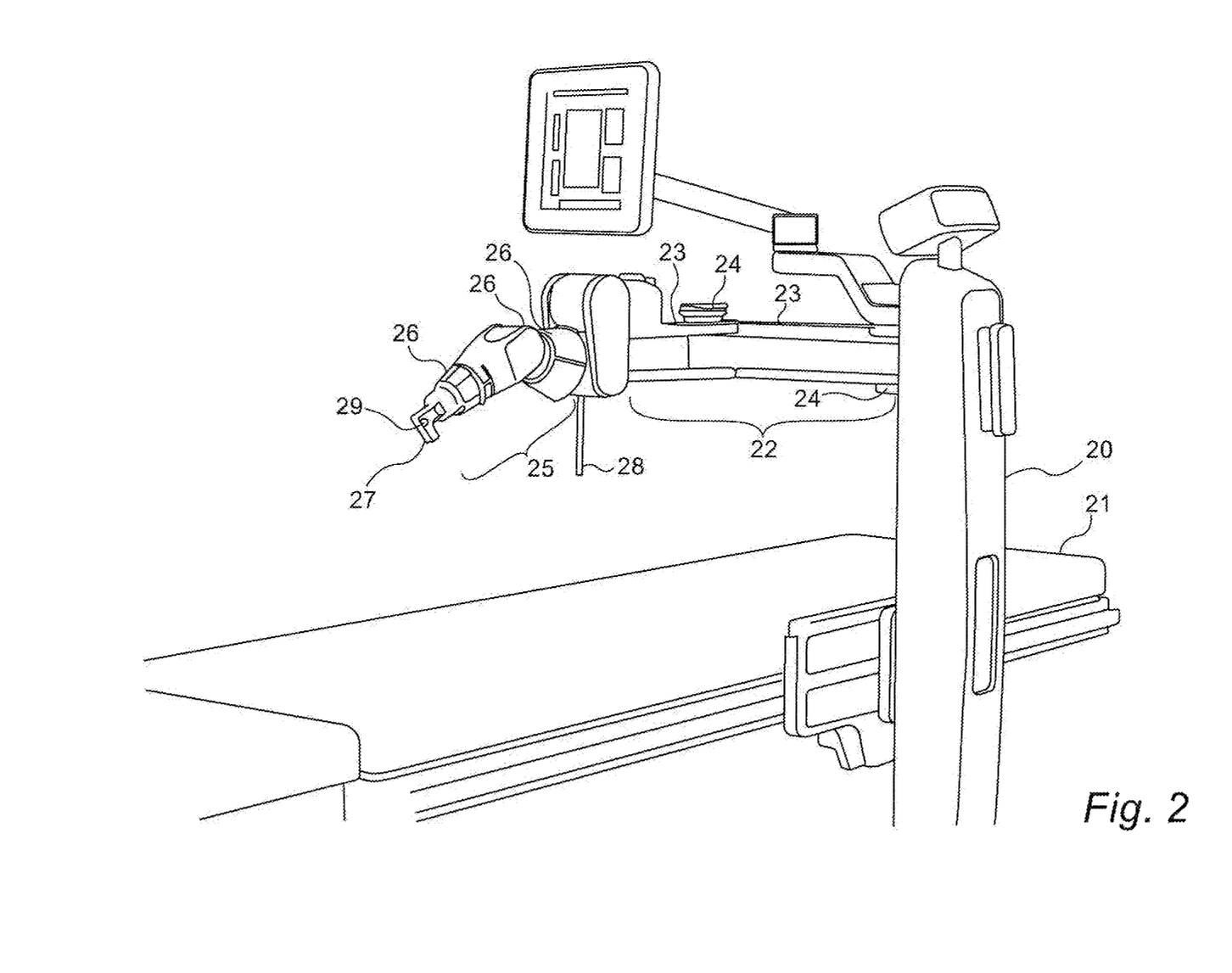
FIG. 2 to FIG. 4 are schematic isometric views of an alternative robotic surgical system in which the robotic base is connected by means of a support post to the operating table.
Figure 3:
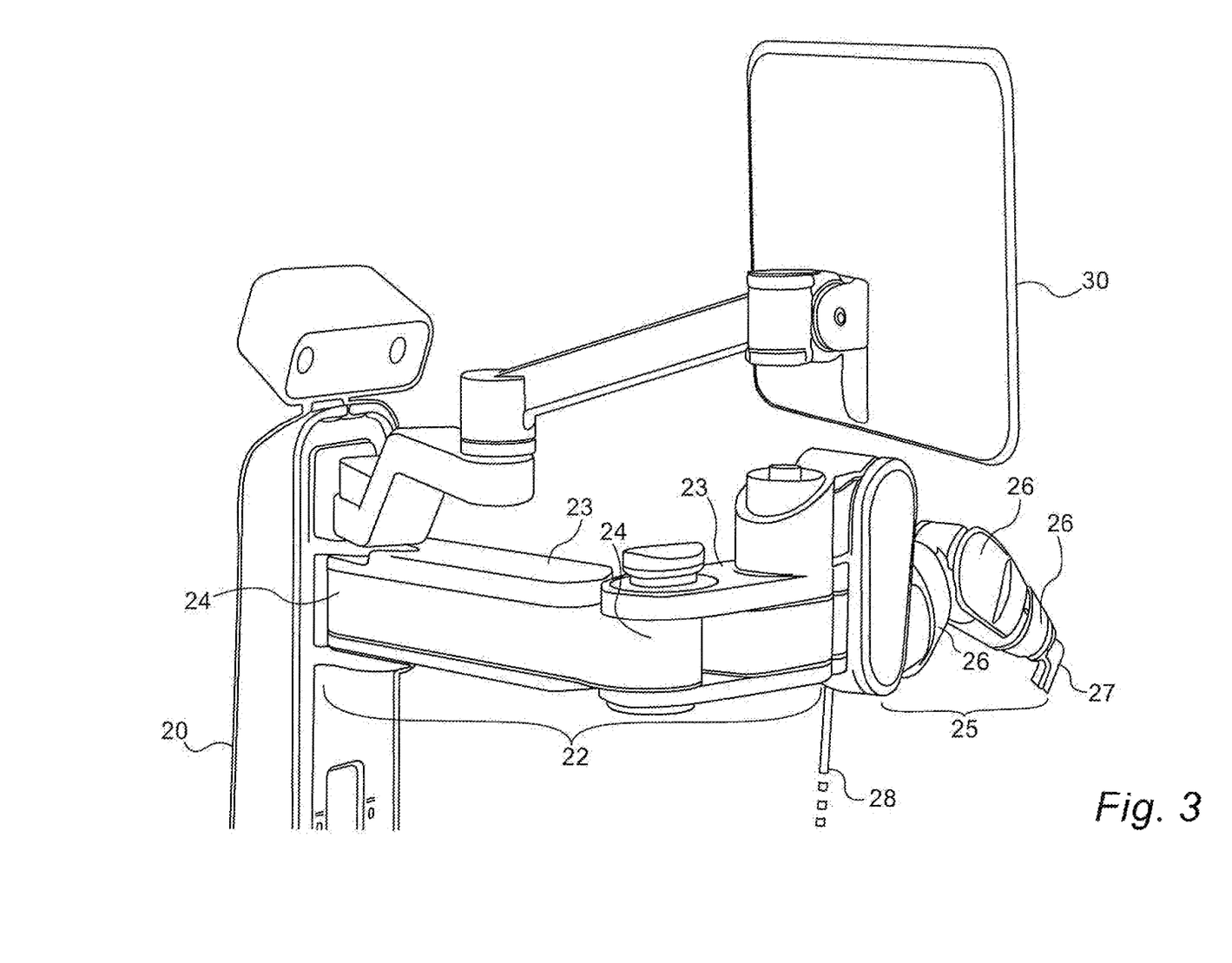
Figure 4:
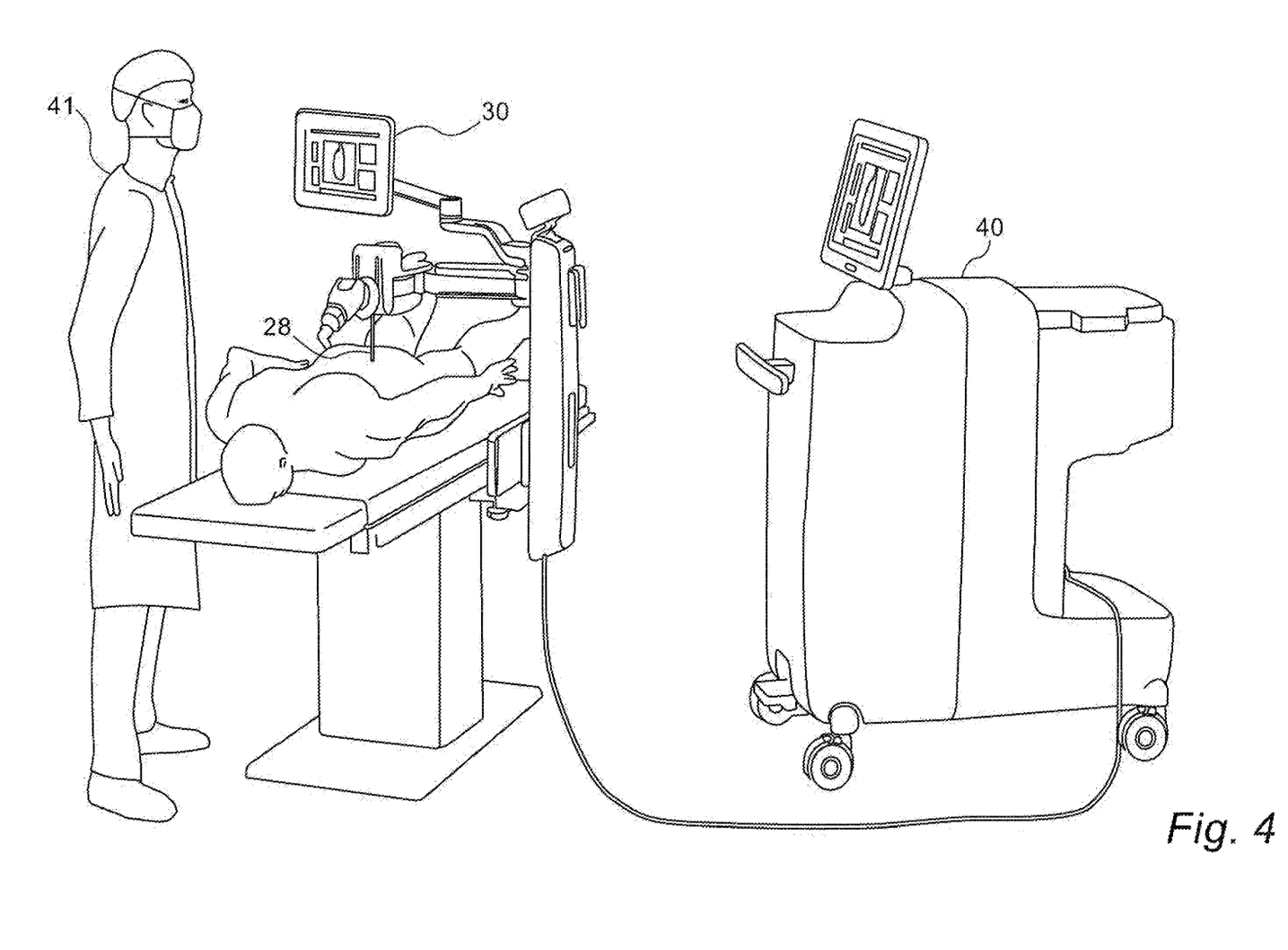

In FIG. 1, the robot base 12 is shown as a floor mounted base, but it is be understood that the robot base could be attached to a support post attached to the operating table, as shown in FIGS. 2 to 4 hereinbelow, or any other feature in the vicinity, such as the ceiling over the operating table. The base may even be supported on a cart. Although such a cart should be locked in position in order to ensure safe operation, the natural flexibility of a cart amounted robot, as compared with a bed or floor mounted robot, may contribute in part to the intentionally incorporated flexibility of the base system. In such a configuration, the true base may be considered to be the wheels of the cart locked on the floor of the Operating Room, while the cart itself may be considered to be part of the robotic base arm.

Additionally, even a support post or similar can have an intrinsic flexibility, such that it may also be considered to be part of the flexible mechanical path between the base and the bone connection link 13.

In the implementation shown in FIG. 1, the bone connection link can be either a static rod, or it can include an automated bone connection unit 10, as described in the above mentioned International Published Patent Application WO2015/087335.

A three dimensional X-ray target (not shown) can be held by the robotic actuator arm, such that a fluoroscopic X-ray image of the region of interest including the target, can be used for registration of the robotic frame of reference to any preoperative images used in planning the surgery.

Reference is now made to FIG. 2, which is a schematic isometric view of an alternative robotic surgical system in which the robotic base is connected by means of a support post 20 to the operating table 21. The robotic arm has two sections:

(i) a robotic base arm section 22 comprising struts 23 and rotary and prismatic joints 24, whose flexibility, together with the bending of the support post 20, which should therefore also be considered part of the robotic base arm, provide the base arm section with the desired extent of flexibility, and (ii) a robotic actuator arm section 25, which is a very rigidly constructed section, made up in this exemplary system, of several rotary joints 26 and the end actuator 27 itself. If a larger robotic work envelope is desired, additional links may be incorporated between the rotary joints 26.

The bone connection link 28 is shown attached to its fixation location between the base arm section 22 and the robotic actuator arm section 25. At its distal end, there may be a bone connecting component, such as a clamp or a pointed or threaded end such as a k-wire. Additionally, the bone connection link 28 may incorporate an automated bone connection unit such as that shown in FIG. 1. The optical scanning head 29, which may be a small sensor device, is mounted in a position where it can scan the surface as the robot arm moves, such as at the end of the actuator arm 27. An optional navigation camera is shown mounted on the support post 20, in order to track items such as surgical tools, even if not involved in navigating them to their target. The robotic base may be connected to the bed through a mechanism that "floats" the robot base and arm so that the nurse can attach it easily to the bed.

Reference is now made to FIG. 3, which is an additional view of the system shown in FIG. 2, showing the parts described in FIG. 2 from an alternative vantage point. A display screen 30 is also shown for providing information to the surgeon performing the operation.

Reference is now made to FIG. 4, which is a further schematic drawing showing an operation in progress with the system control cart 40, and the surgeon 41 surveying the data on the operating table screen 30. The bone connection link 28 is shown attaching the junction of the base arm section and the robotic actuator arm section to a point in the lower spine of the patient.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A robotic surgical system, comprising:
a base for fixing the system relative to an operating table;
an end actuator for enabling alignment of a surgical tool for performing a procedure on a subject on the operating table;
a set of robotically actuated arms connected between the base and the end actuator, the set comprising:
a first section connected at an end to the base; and
a second section connected to the first section remotely from the end, and having the end actuator at an end region remote from the second section connection to the first section; and
a coupling point between the first section and the second section, adapted to be attached to a part of the subject's anatomy through a connection element;
wherein the first section is configured to have a predetermined level of mechanical rigidity less than that of the second section.

2. The robotic surgical system of claim 1, wherein the predetermined mechanical rigidity of the first section arises at least in part from a predetermined rigidity of at least one link of the first section.

3. The robotic surgical system of claim 1, wherein the predetermined mechanical rigidity of the first section arises at least in part from a predetermined stiffness of at least one joint of the first section.

4. The robotic surgical system of claim 3, wherein the predetermined stiffness of the at least one joint of the first section is predetermined by control of a gain of an electronic circuit controlling the joint.

5. The robotic surgical system of claim 4, wherein the predetermined mechanical rigidity of the first section is adjusted electronically according to an expected motion of the part of the subject's anatomy.

6. The robotic surgical system of claim 4, wherein the predetermined mechanical rigidity of the first section is adjusted electronically according to an expected pose of the first section.

7. The robotic surgical system of claim 1, wherein the connection element is connected to a junction region between the first section and the second section of the set of robotically actuated arms.

8. The robotic surgical system of claim 1, wherein the connection element is connected to a component situated between the first section and the second section of the set of robotically actuated arms.

9. The robotic surgical system of claim 1, wherein the connection element is connected to a junction between the first section and the second section of the set of robotically actuated arms.

10. The robotic surgical system of claim 1, wherein the first section of the set of robotically actuated arms has at least one joint configured to have a reduced level of rigidity in comparison with a maximum rigidity attainable in such a type of joint, such that the predetermined mechanical rigidity of the first section is less than that of the second section.

11. The robotic surgical system of claim 10, wherein the reduced level of rigidity of the at least one joint is generated by reducing a gain of a control circuit associated with the at least one joint.

12. The robotic surgical system of claim 1, wherein the first section of the set of robotically actuated arms has at least one arm member configured to have a reduced level of stiffness in comparison with a maximum stiffness attainable in such a type of arm member, such that the predetermined mechanical rigidity of the first section is less than that of the second section of the set of robotically actuated arms.

13. The robotic surgical system of claim 1, wherein the second section of the set of robotically actuated arms has sufficient rigidity that a position of the end actuator relative to a location of the point coupled to the connection element is maintained within a level which is determined to achieve a required accuracy of the procedure.

14. The robotic surgical system of claim 1, further comprising an optical scanning system for detection of a position of the subject, and wherein a position of the set of robotically actuated arms is controlled based at least in part on the detected position of the subject in order to prevent collision of the set of robotically actuated arms with the subject or with an implantation accessory.

15. The robotic surgical system of claim 14, wherein the optical scanning system is located either on the set of robotically actuated arms, or on a static point in a vicinity of the set of robotically actuated arms.

16. The robotic surgical system of claim 15, wherein the predetermined mechanical rigidity of the first section is sufficiently less than that of the second section to enable the part of the subject's anatomy coupled to the connection element to move by up to an extent of estimated motion of the subject without becoming uncoupled from the connection element.

17. The robotic surgical system of claim 16, wherein the part of the subject's anatomy coupled to the connection element can move with three directions of freedom.

18. The robotic surgical system of claim 1, wherein the connection element is switchable between a rigid state and a released state, the released state allowing longitudinal extension of the connection element, the system further comprising a force sensor such that the connection element switches from the rigid state to the released state when a sensed force along the connection element exceeds a predetermined level.

19. The robotic surgical system of claim 18, wherein the predetermined mechanical rigidity of the first section compared to that of the second section is such that the part of the subject's anatomy coupled to the connection element can move by up to an estimated extent of motion of the subject before the connection element switches between the rigid state and the released state.

20. The robotic surgical system of claim 18, wherein the part of the subject's anatomy is the subject's sternum, and the predetermined level of the sensed force is such that the subject's sternum can move by up to 12 mm before the predetermined level of force is reached.

21. The robotic surgical system of claim 18, wherein the connection element is adapted to reconnect after release, at a known position.

22. The robotic surgical system of claim 1, wherein the predetermined mechanical rigidity of the first section is configured to be less than that of the second section, so that the coupling point between the first section and the second section is enabled to move with motion of the part of the subject's anatomy.

23. A method of performing spinal surgery on a subject, comprising:
  laying a subject in a lateral position on an operating table;
  providing a robotic surgical system having an operating envelope that can enable a surgical tool to reach both the lateral side of the subject and the posterior spinal position, the robotic surgical system comprising:
    a base for fixing the robotic surgical system relative to the operating table;
    an end actuator for enabling alignment of a surgical tool;
    a set of robotically actuated arms connected between the base and the end actuator, the set comprising:
      a first section connected at an end to the base; and
      a second section connected to the first section remotely from the end, and having the end actuator at an end region remote from the second section connection to the first section; and
    a coupling point between the first section and the second section, adapted to be attached to a part of the subject's anatomy through a connection element;
    wherein the first section is configured to have a predetermined level of mechanical rigidity less than that of the second section;
  performing a robotic Lateral Interbody Fusion procedure on the subject laying in the lateral position; and
  directing the robotic surgical system to perform a percutaneous posterior spinal procedure,
  wherein both of the procedures are performed without a need to move the subject.

24. A robotic surgical system comprising:
  a base of a robot located in a fixed position relative to an operating table;
  a controlled activating arm of the robot, adapted to enable alignment of a surgical tool for performing a surgical procedure; and
  a point of a attachment of the robot, adapted to be attached by means of a connection element to a part of an anatomy of a subject on the operating table, the point of attachment also supporting the controlled activating arm and being attached to the base by means of at least one robotic element,
  wherein the at least one robotic element has a predetermined level of mechanical flexibility greater that of the controlled activating arm, the predetermined level of mechanical flexibility providing the point of attachment with a range of free motion.

25. The robotic surgical system of claim 24, wherein any movement of the connection element moves the controlled activating arm equally.

26. The robotic surgical system of claim 24, wherein motion of the part of the subject's anatomy is transferred to the point of attachment point through the connection element.

* * * * *